(12) United States Patent
Zhang et al.

(10) Patent No.: US 10,206,402 B2
(45) Date of Patent: Feb. 19, 2019

(54) ENVIRONMENTALLY-FRIENDLY EMAMECTIN BENZOATE PREPARATION AND PREPARATION METHOD THEREFOR

(71) Applicant: NANJING SCIENX BIOLOGICAL TECHNOLOGY CO., LTD, Jiangsu (CN)

(72) Inventors: Ziyong Zhang, Guangzhou (CN); Bing Liang, Guangzhou (CN)

(73) Assignee: NANJING SCIENX BIOLOGICAL TECHNOLOGY CO., LTD., Jiangsu (CN)

( * ) Notice: Subject to any disclaimer, the term of this patent is extended or adjusted under 35 U.S.C. 154(b) by 165 days.

(21) Appl. No.: 15/118,825

(22) PCT Filed: Feb. 9, 2015

(86) PCT No.: PCT/CN2015/072545
§ 371 (c)(1),
(2) Date: Aug. 12, 2016

(87) PCT Pub. No.: WO2015/120786
PCT Pub. Date: Aug. 20, 2015

(65) Prior Publication Data
US 2017/0049107 A1    Feb. 23, 2017

(30) Foreign Application Priority Data

Feb. 14, 2014  (CN) .......................... 2014 1 0051692
Feb. 14, 2014  (CN) .......................... 2014 1 0052149
Feb. 14, 2014  (CN) .......................... 2014 1 0052228

(51) Int. Cl.
*A01N 43/90* (2006.01)
*A01N 25/02* (2006.01)
*A01N 25/22* (2006.01)
*A01N 25/24* (2006.01)
*A01N 25/30* (2006.01)

(52) U.S. Cl.
CPC ............. *A01N 43/90* (2013.01); *A01N 25/02* (2013.01); *A01N 25/22* (2013.01); *A01N 25/24* (2013.01); *A01N 25/30* (2013.01)

(58) Field of Classification Search
CPC ........ A01N 43/90; A01N 25/30; A01N 25/24; A01N 25/22; A01N 25/02
USPC ............................................ 504/100; 514/30
See application file for complete search history.

(56) References Cited

FOREIGN PATENT DOCUMENTS

| CN | 101485322 A | | 7/2009 |
| CN | 101731207 | * | 6/2010 |
| CN | 102475084 A | | 5/2012 |
| CN | 102669187 A | | 9/2012 |

OTHER PUBLICATIONS

Kaiyun Wang, Pesticide Preparation, Aug. 31, 2009, pp. 130-131, China Agricultural Press, China.
Zhu Xiaobing, et al., Application of Surfactant in Pesticide Water Agent, Shandong Pesticide Information, Dec. 18, 2009, pp. 31-32, China Academic Journal Electronic Publishing House www.cnki.net, China.
Yu Zhang, et al., Relationship Between HLB Value of Anionic Surfactants and Terminal Group and Carbon Atom Number, Inner Mongolia Petrochemical Technology, Aug. 25, 2004, pp. 4-5, vol. 30, China Academic Journal Electronic Publishing House www.cnki.net, China.
www.agrichem.cn, 5% Emamectin Benzoate Soluble Granule, Source: Website Forum Dec. 26, 2011, China Pesticide Network www.agrichem.cn http://www.agrichem.cn/news/2011/12/26/201112261322938332.shtml.

* cited by examiner

*Primary Examiner* — Yih-Horng Shiao
(74) *Attorney, Agent, or Firm* — Lewis Roca Rothgerber Christie LLP

(57) ABSTRACT

An environmentally-friendly emamectin benzoate preparation. The environmentally-friendly emamectin benzoate preparation comprises emamectin benzoate and an agent A and does not comprise any organic solvent. The agent A is selected from one or more of an anionic surfactant containing sulfonic acid groups, an anionic surfactant containing sulfuric acid groups, and an anionic surfactant containing carboxy groups. The preparation may further comprise an agent B, a functional agent, a pesticide adjuvant and other ingredients. The preparation is preferably an aqueous solution or water-soluble powder. Also provided is a preparation method for the aqueous solution or water-soluble powder.

29 Claims, 5 Drawing Sheets

ENVIRONMENTALLY-FRIENDLY EMAMECTIN BENZOATE PREPARATION AND PREPARATION METHOD THEREFOR

CROSS-REFERENCE TO RELATED APPLICATIONS

The present application is a National Phase Patent Application of, and claims priority to and the benefit of International Application Number PCT/CN2015/072545, filed Feb. 9, 2015, which claims the benefit of priority to Chinese patent applications NOs. 201410052228.5, 201410051692.2 and 201410052149.4 filed on 14 Feb. 2014, the entire contents of all of which are incorporated herein by reference.

TECHNICAL FIELD

The present invention relates to the field of novel pesticidal formulation. Particularly, the present invention relates to a novel environmentally-friendly formulation of emamectin benzoate and preparation method therefor.

BACKGROUND OF THE INVENTION

With the increased awareness of environmental protection, both efficient and environmentally-friendly demands have been put forward on pesticidal formulation. Studies found that for one particular technical material, effect of a pesticidal formulation comprising the technical material depends on the form of the formulation, and dispersion state and size of technical material particles. Scientific knowledge tells us that, when other conditions are identical, the smaller the sizes of technical material particles are, the greater a surface area formed is, and the larger a contact area with plant leaves and pests is. Based on those, a better efficacy will be achieved by the pesticide, and thus the amount of pesticide used will be reduced accordingly.

Standards for evaluating whether a pesticidal formulation is environmentally-friendly or not relate to not only the properties of the technical material itself, but also whether organic solvents are used in the formulation, and whether the solvents and additives used are environmentally-friendly as well. Although various water-based pesticidal formulations are generally environmentally-friendly formulation, how friendly they are to the environment should be evaluated by reference to the above standards.

Among water-based pesticidal formulations, only pesticidal technical material in a water solution (aqueous solution) is dispersed at the level of single molecules, and has minimum size. However, there are only few pesticides that can be processed as aqueous solution and some of them hydrolyze easily in water, which limits the application of aqueous solution in pesticidal formulation. Most pesticides are oil soluble, some of which can only be dissolved in organic solvents, and some of which are even difficult to be dissolved in commonly used organic solvents. Therefore, water-based formulations comprising those pesticides can only be prepared generally into micro-emulsion (ME), emulsion (EW), aqueous suspension concentrate (SC) and aqueous suspo-emulsion (SE). The particle size of pesticidal technical material, when is dispersed in water, increases in turn among the four formulations. Micro-emulsion and emulsion are systems that droplets of pesticidal technical material dissolved in organic solvent are dispersed homogeneously in water; wherein the micro-emulsion has the smallest droplets of lower than 100 nm in size which is less than ¼ of visible light wavelength, thus the micro-emulsion system is transparent and thermodynamically stable. Emulsion has droplets of a few hundred nanometers to microns or above in size, which is close to or even greater than visible light wavelength, thus the emulsion system is opaque and lacks stability. The aqueous suspension concentrate is a system that pesticidal particles, which have been crushed into micron size, are suspended in the water through the action of the macromolecular dispersing agent. This kind of system has a tendency to have pesticidal grains condensed. The aqueous suspo-emulsion is a combination of aqueous suspension concentrate and emulsion. All the above four formulations, expect the aqueous suspo-emulsion, have 10%-20% organic solvent which may reduce their environmental friendliness to different degrees.

Emamectin benzoate (EB) has a structure as shown in formula 2. Emamectin benzoate is a super-effective insecticide and acaricide that is obtained starting from avermectin B1a, one biological antibiotic pesticide, by means of chemical modification. Based on the super-effective, wide-spectral, almost non-toxic, and non-residual advantages, as well as little resistance of emamectin benzoate, the insecticidal activity of it is dozens of times that of the parent avermectin B1a. Results of efficacy experiments show that emamectin benzoate has an activity for many pests that cannot be achieved by other pesticides. Emamectin benzoate is super-effective especially for pests from the orders Lepidoptera and Diptera, and said pests comprise redbanded leafroller, *Heliothis virescens*, cotton bollworm, *Manduca sexta*, *Plutella xylostella* L. *Spodoptera littoralis*, *Spodoptera exigua*, *Spodoptera frugiperda*, *Trichoplusis ni* (Hubner), *Argyrogramma agnata*, *Pieris rapae Linnaeus*, *Hellula undalis*, *Hellula undalis Fabricius*, *Manduca quinquemaculata*, *Leptinotarsa decemlineata*, *Epilachna varivestis* and the like. Emamectin benzoate works wonders on resistance cotton bollworm and *Plutella xylostella*, and it has a good insecticidal effect even at very low doses. Therefore, with the prohibition of use of highly toxic pesticide, emamectin benzoate has become a mainstream product of insecticide on the market.

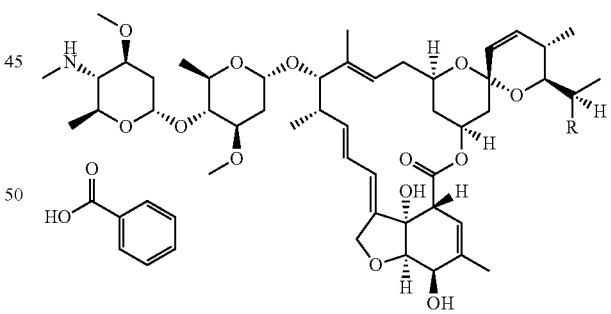

R = Me or Et

Emamectin benzoate is easily soluble in various organic solvents, such as acetone, methanol, toluene and xylene, but poorly soluble in water, having a water solubility of only about 0.024 g/L (25° C.). Thus, formulations of emamectin benzoate primarily comprise emulsifiable concentrate (EC), micro-emulsion (ME), emulsion (EW), and water dispersible granule (WG) at present. The mass percentage of active ingredient identified in different formulations is from 0.5% to 5%; wherein the highest content of the effective ingredient is 5.7%, which is equivalent to 5.0% emamectin benzoate.

In the prior art, formulations that use emamectin benzoate as the pesticidal technical material comprise:

Chinese application for invention No. 200710009947.9 discloses a micro-emulsion of emamectin benzoate, wherein components in percentage by weight are: 0.5-5% of emamectin benzoate, 5-20% of solvent, 1-10% of solubilizing assistant, 5-30% of emulsifying agent, 0.1-3% of synergist, 0.1-3% of stabilizer, and the remainder being water; and wherein the solvent is one or more selected from the group consisting of aromatic hydrocarbyl solvents, cyclohexanone, dimethylformamide, and acetone.

Chinese application for invention No. 200510012996.9 discloses an insecticidal micro-emulsion containing emamectin, wherein components are (weight of the micro-emulsion is 100%): 0.2-10% of emamectin, 10-20% of solvent, 8-15% of emulsifying agent, 1-3% of stabilizer, 2-3% of antifreezing agent, and the remainder being water; and wherein the solvent is one or more selected from the group consisting of methanol, ethanol and cyclohexanone.

Chinese invention patent No. ZL200910111224.9 discloses an emulsion of emamectin benzoate, wherein raw materials in the emamectin in percentage by weight are: 0.5-10% of emamectin benzoate, 2-10% of solvent, 2-10% of emulsifying agent, 0.15-5% of co-emulsifying agent, 0.05-5% of thickening agent, 0.2-5% of antifreezing agent, 0.05-0.8% of defoaming agent, and the remainder being water; and wherein the solvent is xylene.

Chinese invention patent No. ZL200610023384.4 provides an emulsion of emamectin benzoate and the preparation method therefor. Substances with following amounts used as raw materials for the emulsion: in percentage by weight, 0.1-20% of emamectin benzoate, 1-10% of solvent, 1-10% of emulsifying agent, 0.1-5% of thickening agent, 0.5-5% of antifreezing agent, 0.1-1% of defoaming agent, and the remainder being water; wherein the solvent is xylene and/or toluene.

In the preparation of the above micro-emulsions and emulsions, organic solvents, such as methanol, toluene, xylene or the mixture thereof and the like which are toxic and harmful are used for dissolving emamectin benzoate, and then emamectin benzoate dissolved in organic solution is dispersed into water through emulsification by surfactants. Although significantly smaller amounts of organic solvents are used in micro-emulsion or emulsion than used in emulsifiable concentrate, the mass percentage of organic solvents is still up to 10%-20%. That is to say, 100-200 kg of organic solvents (such as xylene etc.) would be used when 1 ton of micro-emulsion or emulsion of emamectin benzoate is produced. Organic solvents used could not be ignored when the production scale of those formulations is large, because environmental pollution will come along with spraying the formulations onto crops.

Chinese application for invention with publication No. CN101361479A (publication date: 11 Feb. 2009) discloses a water dispersible granule of emamectin benzoate. Chinese application for invention with publication No. CN1775027A (publication date: 24 May 2006) discloses an insecticidal water soluble granule containing emamectin benzoate.

Emamectin benzoate in dispersible granule and water soluble granule will suspend in water under the action of macromolecular dispersing agent after adding water thereto. However, this kind of system is thermodynamically unstable, and it has a tendency to have grains condensed and precipitation easily occurs after it is allowed to stand for a period of time. What's more, current production process for dispersible granule and water soluble granule has long process flow, including airflow grinding, kneading, granulating and drying etc., for which corresponding production equipments are needed, leading to an increase in production costs.

Moreover, emamectin benzoate itself may degrade rapidly when exposed to light, thus the work period of ordinary pesticidal formulation containing emamectin benzoate is short, generally about 7 days.

Therefore, there is still a need for a novel and more effective environmentally-friendly formulation of emamectin benzoate.

SUMMARY OF THE INVENTION

Therefore, one purpose of the present invention is to provide a novel environmentally-friendly formulation of emamectin benzoate, so as to overcome deficiencies of the existing techniques. Characteristics of the present formulation which are obviously better than those of existing formulations of emamectin benzoate include: (1) the present formulation is free of any organic solvent; (2) all additives used in the present formulation are environmentally-friendly; (3) the present formulation is a solution per se, or a solution obtained after adding water to the formulation, and both the two solutions are thermodynamically stable, and have physical properties in line with national standards for aqueous solution. In addition, the formulation also has better light stability, wettability and functionality, and it not only can prolong effective period, reduce frequency of application and decrease the amount of pesticide used, but also has roles in improving the efficacy of pesticide, reducing residual toxicity and improving the quality of agricultural products.

Another purpose of the present invention is to provide a preparation method for the above formulation.

Technical Solutions Provided by the Present Invention to Realize the Purposes are as Follows:

An environmentally-friendly formulation of emamectin benzoate which comprises emamectin benzoate and an agent A and comprises no organic solvent, wherein the agent A is one or more selected from the group consisting of anionic surfactant containing sulfonic acid group, anionic surfactant containing sulphuric acid group, and anionic surfactant containing carboxylic acid group.

Preferably, the agent A is one or more selected from the group consisting of straight or branched chain aliphatic hydrocarbyl sulfonic acid and salts thereof, straight or branched chain aliphatic hydrocarbyl ether sulfonic acid and salts thereof, straight or branched chain aliphatic hydrocarbyl sulphuric acid and salts thereof, straight or branched chain aliphatic hydrocarbyl ether sulphuric acid and salts thereof, and straight or branched chain aliphatic hydrocarbyl carboxylic acid and salts thereof.

More preferably, the agent A is one or more selected from the group consisting of compounds as shown in Formula 1:

$$CH_3(CH_2)_n(OCH_2CHR')_mRM \qquad (1)$$

wherein, n=7-17, preferably, n=11, 13, 15 or 17;
R'=H or $CH_3$;
R=$-SO_3^-$, $-OSO_3^-$, $-SO_4^-$, $-OSO_4^-$, or $-CO_2^-$;
m=0, 1, 2, 3, or 4;
M=$H^+$, $K^+$, $Na^+$, or $NH_4^{\pm}$.

As a preferred embodiment of the present invention, the agent A is one or more selected from the group consisting of following compounds;

I. dodecyl sulfonic acid, tetradecyl sulfonic acid, hexadecyl sulfonic acid and octadecyl sulfonic acid, and their potassium, sodium or ammonium salts;

II. dodecyl ether sulfonic acid, tetradecyl ether sulfonic acid, hexadecyl ether sulfonic acid and octadecyl ether sulfonic acid, and their potassium, sodium or ammonium salt;

III. dodecyl sulphuric acid, tetradecyl sulphuric acid, hexadecyl sulphuric acid and octadecyl sulphuric acid, and their potassium, sodium or ammonium salts;

IV. dodecyl ether sulphuric acid, tetradecyl ether sulphuric acid, hexadecyl ether sulphuric acid and octadecyl ether sulphuric acid, and their potassium, sodium or ammonium salt;

V. dodecyl carboxylic acid, tetradecyl carboxylic acid, hexadecyl carboxylic acid and octadecyl carboxylic acid, and their potassium, sodium or ammonium salts;

Preferably, the above environmentally-friendly formulation of emamectin benzoate further comprises an agent B which is selected from the group consisting of nonionic surfactant containing ethylene oxide unit, propylene oxide unit or glucose unit, and/or natural high molecular surfactant.

Preferably, the nonionic surfactant is one or more selected from the group consisting of polyoxyethylene, polyoxypropylene, polyvinyl alcohol and polyvinylpyrrolidone. More preferably, the nonionic surfactant is one or more selected from the group consisting of straight chain fatty alcohol polyoxyethylene ether, polyoxyethylene straight chain fatty acid ester, straight chain fatty amine polyoxyethylene ether, sorbitan polyoxyethylene ether fatty acid ester, alkyl polyglycoside and polyoxyethylene castor oil.

Preferably, the natural high molecular surfactant is one or more selected from the group consisting of water soluble starch derivatives, water soluble cellulose derivatives, and chitosan and the derivatives thereof. More preferably, the natural high molecular surfactant is one or more selected from the group consisting of dextrin, carboxymethyl starch, carboxymethyl cellulose, chitosan, carboxymethyl chitosan, and chitosan quaternary ammonium salt.

Preferably, the above environmentally-friendly formulation of emamectin benzoate may further comprises a functionalizing agent which is selected from the group consisting of synthetic chemicals or natural products having a synergic, antibacterial or stress-resistance function, or having a role in stimulating crop growth, improving pesticide efficacy, reducing residual toxicity or improving the quality of agricultural products.

More preferably, the functionalizing agent is one or more selected from the group consisting of tea saponin, humic acid, chitosan and the derivatives thereof, alginate, hyaluronic acid, saponin extract, and matrine.

Further preferably, the above environmentally-friendly formulation of emamectin benzoate further comprises a pesticidal additive.

Preferably, the pesticidal additive comprises a light stabilizer and/or a drift control agent.

Wherein the light stabilizer is one or more selected from the group consisting of salicylate light stabilizer, benzophenone light stabilizer, benzotriazole light stabilizer and hindered amine light stabilizer. More preferably, the light stabilizer is benzophenone light stabilizer. Most preferably, the light stabilizer is one or more selected from the group consisting of 2,4-dihydroxy-5-sulfo benzophenone, 2,2',4, 4'-tetrahydroxy benzophenone, and 2,3,4,4'-tetrahydroxy benzophenone.

Preferably, the drift control agent is selected from the group consisting of water soluble synthetic high molecular materials and water soluble natural high molecular materials, and both of those materials can decrease the surface tension of spray droplets, increase viscoelasticity, increase the deposition of pesticides, and/or reduce the rebounce of droplets. More preferably, the drift control agent is water soluble natural high molecular materials. Most preferably, the drift control agent is one or more selected from the group consisting of water soluble cellulose derivatives, water soluble guar gum and the derivatives thereof, and water soluble starch and the derivatives thereof.

Preferably, the environmentally-friendly formulation of emamectin benzoate of the present invention is an aqueous solution or a water soluble powder.

Preferably, the above environmentally-friendly formulation of emamectin benzoate further comprises a defoaming agent.

Preferably, the defoaming agent is one or more selected from the group consisting of organosilicone defoaming agent, $C_7$-$C_9$ fatty alcohol and tributyl phosphate.

As a preferred embodiment, the present invention provides an environmentally-friendly aqueous solution of emamectin benzoate, in percentage by weight, comprising: 1%-7% of emamectin benzoate, 1%-10% of the agent A, 1%-6% of the agent B, 1%-6% of an antifreezing agent, 0.01%-0.1% of the defoaming agent, and the remainder being water.

As a more preferred embodiment, the present invention provides an environmentally-friendly aqueous solution of emamectin benzoate, in percentage by weight, comprising: 1%-7% of emamectin benzoate, 2%-8% of the agent A, 1%-6% of the agent B, 1%-6% of the antifreezing agent, 0.01%-0.1% of the defoaming agent, and the remainder being water.

As a preferred embodiment, the present invention provides a multifunctional environmentally-friendly aqueous solution of emamectin benzoate, in percentage by weight, comprising: 1%-7% of emamectin benzoate, 1%-10% of the agent A, 1%-6% of the agent B, 1%-5% of the functionalizing agent, 1%-6% of the antifreezing agent, 0.01%-0.1% of the defoaming agent, 0.1-0.4% of the light stabilizer, 1%-3% of the drift control agent, and the remainder being water.

As a more preferred embodiment, the present invention provides a multifunctional environmentally-friendly aqueous solution of emamectin benzoate, in percentage by weight, comprising: 1%-7% of emamectin benzoate, 2%-8% of the agent A, 1%-6% of the agent B, 1%-5% of the functionalizing agent, 1%-6% of the antifreezing agent, 0.01%-0.1% of the defoaming agent, 0.1-0.4% of the light stabilizer, 1%-3% of the drift control agent, and the remainder being water.

As another preferred embodiment, the present invention provides an environmentally-friendly water soluble powder of emamectin benzoate with raw materials including: 1-7 parts by weight of emamectin benzoate, 1-10 parts by weight of the agent A, 1-6 parts by weight of the agent B, and 0.01-0.1 parts by weight of the defoaming agent.

As a more preferred embodiment, the present invention provides an environmentally-friendly water soluble powder of emamectin benzoate with raw materials including: 1-7 parts by weight of emamectin benzoate, 2-8 parts by weight of the agent A, 1-6 parts by weight of the agent B, and 0.01-0.1 parts by weight of the defoaming agent.

As a preferred embodiment, the present invention provides a multifunctional environmentally-friendly water soluble powder of emamectin benzoate with raw materials including: 1-7 parts by weight of emamectin benzoate, 1-10 parts by weight of the agent A, 1-6 parts by weight of the agent B, 1-5 parts by weight of the functionalizing agent, 0.1-0.4 parts by weight of the light stabilizer, 1-3 parts by weight of the drift control agent, and 0.01-0.1 parts by weight of the defoaming agent.

As a more preferred embodiment, the present invention provides a multifunctional environmentally-friendly water soluble powder of emamectin benzoate with raw materials including: 1-7 parts by weight of emamectin benzoate, 2-8 parts by weight of the agent A, 1-6 parts by weight of the agent B, 1-5 parts by weight of the functionalizing agent, 0.1-0.4 parts by weight of the light stabilizer, 1-3 parts by weight of the drift control agent, and 0.01-0.1 parts by weight of the defoaming agent.

The agent A, the agent B, the functionalizing agent, the light stabilizer, the drift control agent and the defoaming agent used in the above preferred embodiments are as defined above. The antifreezing agent is one or more selected from the group consisting of ethylene glycol, propylene glycol, glycerol, low-molecular-weight polyethylene glycol and sorbitol. Preferably, glycerol, ethylene glycol and propylene glycol which are easy to degrade are more preferred in consideration of environmental friendliness.

Another purpose of the present invention is to provide a method for preparing the environmentally-friendly aqueous solution of emamectin benzoate, comprising the following steps:
I. preparing respective raw materials in accordance with the composition of the formulation to be prepared;
II. adding all the other raw materials including the agent A, except for emamectin benzoate, the defoaming agent and the water, to a stirred tank, and then pouring part of the water to the stirred tank, and stirring until the materials dissolved, thereby obtaining solution A;
III. adding emamectin benzoate to the solution A, and stirring until dissolved, thereby obtaining solution B; and
IV. adding the residual water to the solution B, stirring, and then adding the defoaming agent, stirring slightly, and standing before filtration.

Yet another purpose of the present invention is to provide a method for preparing the multifunctional environmentally-friendly aqueous solution of emamectin benzoate, comprising the following steps:
I. preparing respective raw materials in parts of weight in accordance with the composition of the formulation to be prepared;
II. adding all the other raw materials including the agent A, except for emamectin benzoate, the defoaming agent, the pesticidal additive and the water, to a stirred tank, and pouring part of the water to the stirred tank, and stirring until the materials dissolved, thereby obtaining solution A;
III. adding emamectin benzoate to the solution A, stirring until dissolved, thereby obtaining solution B; and
IV. adding the pesticidal additive and the residual water to the solution B, stirring until the pesticidal additive dissolved, and then adding the defoaming agent, stirring slightly, and standing before filtration.

Still another purpose of the present invention is to provide a method for preparing the environmentally-friendly water soluble powder of emamectin benzoate or the multifunctional environmentally-friendly water soluble powder of emamectin benzoate, comprising the following process I and process II:
process I: mixing all the raw materials including emamectin benzoate homogeneously; or
process II: dissolving the agent A in water, and then adding emamectin benzoate, other raw materials and water to obtain a solution of emamectin benzoate in a concentration in percentage by weight of 1%-7%, and dehydrating the solution.

Preferably, the process II comprises the following steps:
a. preparing respective raw materials in accordance with the composition of the formulation to be prepared;
b. dissolving the agent A in 20-60 parts by weight of water, and stirring until dissolved, thereby obtaining solution A;
c. adding all the other raw materials including emamectin benzoate, except for the defoaming agent, to the solution A, and then adding water to obtain a solution of emamectin benzoate in a concentration in percentage by weight of 1%-7%, and stirring until dissolved, thereby obtaining solution B;
d. adding the defoaming agent to the solution B, stirring slightly, and standing before filtration, thereby obtaining solution C;
e. drying, preferably spray drying the solution C.

Emamectin benzoate is obtained by introducing characteristic group methylamino to the chemical structure of avermectin B1a (a kind of antibiotics) and allowing the group to react with a benzoic acid to form a salt. The solubility in water of emamectin benzoate is poor, only about 0.024 g/L. Therefore, in prior art, emamectin benzoate is usually dissolved in organic solvent(s) firstly, and then formulated into an emulsion or micro-emulsion; or, emamectin benzoate is mixed with a large amount of inert filler(s) and formulated into a solid formulation which is able to suspend in water.

The agent A of the present invention is a substance that can improve the dissolubility and separability of emamectin benzoate in water. Research carried out by the present inventors found that certain particular compounds have that effect, and so an aqueous solution of emamectin benzoate can be formulated without the assistance of organic solvents. Therefore, following screening experiments for preferred agent A have been conducted by the inventors.

Different types of compounds and emamectin benzoate were added into 10 ml of water, and stirred at room temperature. The dissolution behavior of emamectin benzoate was observed to select preferred types for the agent A. The results are shown in Table 1.

TABLE 1

Screening scheme for agent A and results

| Candidate agent | Type | Amount/g | Emamectin benzoate/g | Dissolution behavior |
| --- | --- | --- | --- | --- |
| Sodium dodecyl sulfonate | anionic | 0.5 | 0.2 | Emamectin benzoate was dispersed gradually and dissolved completely |
| Ammonium tetradecyl sulphate | anionic | 0.5 | 0.2 | Emamectin benzoate was dispersed gradually and dissolved completely |

TABLE 1-continued

Screening scheme for agent A and results

| Candidate agent | Type | Amount/g | Emamectin benzoate/g | Dissolution behavior |
|---|---|---|---|---|
| Sodium stearate | anionic | 0.5 | 0.2 | Emamectin benzoate was dispersed gradually and most of it was dissolved |
| Polyoxyethylene dodecyl ether | nonionic | 0.5 | 0.2 | Part of emamectin benzoate was dissolved |
| Polyoxyethylene stearate | nonionic | 0.5 | 0.2 | Part of emamectin benzoate was dissolved |
| Alkyl polyglycoside | nonionic | 0.5 | 0.2 | A small amount of emamectin benzoate was dissolved |
| Chitosan hydrochloride | cationic | 0.5 | 0.2 | A small amount of emamectin benzoate was dissolved |
| Carboxymethyl chitosan | zwitterionic | 0.5 | 0.2 | A small amount of emamectin benzoate was dissolved |

The results of the above experiments showed that the agent A is preferably anionic surfactant containing sulfonic acid group, anionic surfactant containing sulphuric acid group, or anionic surfactant containing carboxylic acid group.

What's more, results of further experiments showed that agent A is more preferably selected from the group consisting of straight or branched chain aliphatic hydrocarbyl sulfonic acid and salts thereof, straight or branched chain aliphatic hydrocarbyl ether sulfonic acid and salts thereof, straight or branched chain aliphatic hydrocarbyl sulphuric acid and salts thereof, straight or branched chain aliphatic hydrocarbyl ether sulphuric acid and salts thereof, and straight or branched chain aliphatic hydrocarbyl carboxylic acid and salts thereof.

Most preferably, the agent A is selected from the group consisting of compounds as shown in formula 1:

$$CH_3(CH_2)_n(OCH_2CHR')_mRM \quad (1)$$

wherein, n=7-17, preferably, n=11, 13, 15 or 17;
R'=H or $CH_3$;
R=—$SO_3^-$, —$OSO_3^-$, —$SO_4^-$, —$OSO_4^-$, or —$CO_2^-$;
m=0, 1, 2, 3, or 4;
M=$H^+$, $K^+$, $Na^+$, or $NH_4^\pm$.

In the present invention, the solubility of emamectin benzoate in water is improved by two orders of magnitude by combining emamectin benzoate and the preferred agent A, and thus a stable and concentrated emamectin benzoate water solution is obtained. In addition, the agent B is used to improve the dispersity of emamectin benzoate in water, enhance the stability and the resistance to hard water of the formulation, decrease the surface tension of the formulation when it is diluted, and increase the spreadability of the formulation on plant leaves. On this basis, the present invention provides a novel environmentally-friendly formulation of emamectin benzoate.

The environmentally-friendly aqueous solution of emamectin benzoate provided by the present invention is not a micro-emulsion which exists in the prior art, because no any organic solvent is used during the preparation of the present aqueous solution. All micro-emulsions and aqueous solutions of emamectin benzoate in the prior art are systems formed by dispersing droplets of organic solvent(s) in which emamectin benzoate is dissolved in water. When emamectin benzoate in xylene was dispersed to the aqueous solution system of the present invention without emamectin benzoate, oil-water separation happened and no uniform and stable system was formed. It showed that the aqueous solution of the present invention is not a traditional micro-emulsion. Testing showed that various performances and parameters of the aqueous solution of the present invention reached national standards:

(1) The aqueous solution is uniform and clear in appearance and stable in storage, and the appearance of this formulation does not change after being placed in room temperature for 2 years; what's more, the aqueous solution can be dispersed and diluted in water in any ratio.

(2) Content of the active ingredient emamectin benzoate in the aqueous solution can be up to 1%-7%, which is equal to or higher than that of other liquid formulations currently in China.

(3) The hard-water resistance of the aqueous solution is qualified and no turbidness and precipitation will form when the aqueous solution is mixed with hard water with standard concentration.

(4) High- and low-temperature resistance of the aqueous solution is qualified.

The average particle size of the water soluble powder of emamectin benzoate prepared by the preferred method of the present invention can be controlled within 50 μm-150 μm. What's more, the content of the active ingredient emamectin benzoate in the water soluble powder can be controlled in the range of 15%-35% by adjusting the amount of additives used. A certain amount water soluble power of emamectin benzoate of the present invention is homogeneously added to the corresponding water, depending on different spraying concentrations required by different crops. Then the water soluble power can be quickly dispersed on the surface of the water and infiltrated, and it can be completely dissolved in water with stirring slightly. Then a clear and transparent solution which can be sprayed directly is obtained.

Both the aqueous solution and the water soluble power of the present invention can be prepared at room temperature using generic production equipment for water-based pesticidal formulations, with a strong operability. Moreover, the water soluble power of the present invention can be prepared by mixing the raw materials directly. However, after water is added, the water soluble power prepared by mixing directly needs a long time of stirring before a clear solution is obtained. Therefore, for ease of use, a preferred method for preparing the present water soluble power is that the raw materials are formulated into an aqueous solution, and then the water is removed, then, a solid power is obtained.

The formulation of emamectin benzoate of the present invention can be used to control pests including Lepidoptera, Diptera, Homoptera and Coleoptera pests and the like for crops, such as vegetables, fruits, tea, rice, corn, cotton etc. The persistency of the present aqueous solution is obviously better than that of commercially available emulsifiable concentrate. Therefore, the spraying amount and frequency can be reduced, leading to reduced total quantity of emamectin benzoate, which is more helpful for environment protection.

BRIEF DESCRIPTION OF THE DRAWINGS

Hereinafter, the present invention will be described with reference to the accompanying drawings in detail, wherein:

FIG. 8 is photographs showing experimental results of Experiment 2, which show the dissolution process of the multifunctional environmentally-friendly water soluble power of emamectin benzoate prepared in Example 16, wherein:

DETAILED DESCRIPTION OF THE INVENTION

The present invention will be further described in detail in combination with the embodiments hereinafter. However, the present invention is not limited to the following examples.

Raw materials used in the following examples, unless otherwise specified, are commercially available.

Example 1: A 1% Environmentally-Friendly Aqueous Solution of Emamectin Benzoate

Raw material ratio is:

| | |
|---|---|
| emamectin benzoate | 1.0% (in percentage by weight, as follows); |
| sodium dodecyl sulfonate | 1.5%; |
| polyoxyethylene castor oil (EL-40) | 0.5%; |
| carboxymethyl starch | 0.5%; |
| glycerol | 5%; |
| tributyl phosphate | 0.02%; and |
| deionized water | the remainder. |

It was prepared by the following method:
I. Raw materials which were used to prepare 1000 kg of aqueous solution were prepared in accordance with the raw material ratio;
II. Sodium dodecyl sulfonate, polyoxyethylene castor oil (EL-40), carboxymethyl starch and glycerol were added to a stirred tank, and then part of the deionized water was poured in the stirred tank, and stirred until the materials dissolved, thereby obtaining solution A;
III. Emamectin benzoate was added to the solution A, and stirred until dissolved, thereby obtaining solution B;
IV. The residual deionized water was added to the solution B and stirred, and then the defoaming agent tributyl phosphate was added in, stirred slightly, allowed to stand still, and filtered, thereby obtaining the title product with transparent appearance. Sample of the product was shown in FIG. 1.

Example 2: A 2% Environmentally-Friendly Aqueous Solution of Emamectin Benzoate

Raw material ratio is:

| | |
|---|---|
| emamectin benzoate | 2.0%; |
| ammonium dodecyl sulphate | 3.0%; |
| fatty alcohol polyoxyethylene ether (AEO-09) | 1.0%; |
| carboxymethyl cellulose | 1.0%; |
| propylene glycol | 4.5%; |
| tributyl phosphate | 0.02%; and |
| deionized water | the remainder. |

1000 kg of the title product was obtained by a method similar to that described in Example 1.

Example 3: A 3% Environmentally-Friendly Aqueous Solution of Emamectin Benzoate

Raw material ratio is:

| | |
|---|---|
| emamectin benzoate | 3.0%; |
| ammonium tetradecyl sulphate | 4.5%; |
| alkyl polyglycoside | 1.0%; |
| fatty alcohol polyoxyethylene ether (AEO-15) | 1.0%; |
| carboxymethyl starch | 1.0%; |
| glycerol | 4.5%; |
| organosilicone defoaming agent | 0.02%; and |
| deionized water | the remainder. |

Figure 1:
FIG. 1 is a photograph of the environmentally-friendly aqueous solutions of emamectin benzoate prepared in Examples 1, 3 and 5. In the photograph, from left to right are the environmentally-friendly aqueous solution of emamectin benzoate prepared in Example 1, the environmentally-friendly aqueous solution of emamectin benzoate prepared in Example 3, and the environmentally-friendly aqueous solution of emamectin benzoate prepared in Example 5.

1000 kg of the title product was obtained by a method similar to that described in Example 1, and sample of the product was shown in FIG. 1.

Example 4: A 4% Environmentally-Friendly Aqueous Solution of Emamectin Benzoate Raw material ratio is:

| | |
|---|---|
| emamectin benzoate | 4.0%; |
| sodium tetradecyl ether sulfonate | 6.0%; |
| alkyl polyglycoside | 1.0%; |
| polyoxyethylene castor oil (EL-40) | 2.0%; |
| polyvinyl alcohol | 1.0%; |
| ethylene glycol | 4.0%; |
| organosilicone defoaming agent | 0.02%; and |
| deionized water | the remainder. |

1000 kg of the title product was obtained by a method similar to that described in Example 1.

Example 5: A 5% Environmentally-Friendly Aqueous Solution of Emamectin Benzoate Raw material ratio is:

| | |
|---|---|
| emamectin benzoate | 5.0%; |
| potassium hexadecyl ether sulphate | 7.5%; |
| alkyl polyglycoside | 2.0%; |
| fatty alcohol polyoxyethylene ether (AEO-20) | 2.0%; |
| carboxymethyl cellulose | 1.0%; |
| glycerol | 4.0%; |
| organosilicone defoaming agent | 0.02%; and |
| deionized water | the remainder. |

1000 kg of the title product was obtained by a method similar to that described in Example 1, and sample of the product was shown in FIG. 1.

Example 6: A 7% Environmentally-Friendly Aqueous Solution of Emamectin Benzoate Raw material ratio is:

| | |
|---|---|
| emamectin benzoate | 7.0%; |
| sodium ricinoleate | 3.0%; |
| sodium tetradecyl sulphate | 7.0%; |
| Fatty alcohol polyoxyethylene ether (AEO-20) | 2.0%; |
| carboxymethyl chitosan | 2.0%; |
| ethylene glycol | 3.0%; |
| organosilicone defoaming agent | 0.02%; and |
| deionized water | the remainder. |

1000 kg of the title product was obtained by a method similar to that described in Example 1.

Example 7: A 1% Environmentally-Friendly Aqueous Solution of Emamectin Benzoate Raw material ratio is:

| | |
|---|---|
| emamectin benzoate | 1.0% (in percentage by weight, as follows); |
| potassium oleate | 1.5%; |
| polyoxyethylene castor oil (EL-40) | 0.5%; |
| carboxymethyl starch | 0.5%; |
| glycerol | 5.0%; |
| tributyl phosphate | 0.02%; and |
| deionized water | the remainder. |

1000 kg of the title product was obtained by a method similar to that described in Example 1.

Example 8: A 3% Environmentally-Friendly Aqueous Solution of Emamectin Benzoate Raw material ratio is:

| | |
|---|---|
| emamectin benzoate | 3.0%; |
| sodium ricinoleate | 1.5%; |
| ammonium tetradecyl sulphate | 3.0%; |
| alkyl polyglycoside | 1.0%; |
| fatty alcohol polyoxyethylene ether (AEO-15) | 1.0%; |
| carboxymethyl starch | 1.0%; |
| glycerol | 4.5%; |
| organosilicone defoaming agent | 0.02%; and |
| deionized water | the remainder. |

1000 kg of the title product was obtained by a method similar to that described in Example 1.

Example 9: A 1% Multifunctional Environmentally-Friendly Aqueous Solution of Emamectin Benzoate Raw material ratio is:

| | |
|---|---|
| emamectin benzoate | 1.0% (in percentage by weight, as follows); |
| sodium dodecyl sulfonate | 1.5%; |
| polyoxyethylene castor oil (EL-40) | 0.5%; |
| fatty alcohol polyoxyethylene ether (AEO-09) | 0.5%; |
| tea saponin | 1%; |
| fulvic acid | 1.5%; |
| chitosan | 0.5%; |
| glycerol | 5%; |
| hydroxyethyl cellulose | 2%; |
| 2,2',4,4'-tetrahydroxy benzophenone | 0.1%; |
| tributyl phosphate | 0.02%; and |
| deionized water | the remainder. |

It was prepared by the following method:

I. Raw materials which were used to prepare 1 kg of multifunctional aqueous solution were prepared in accordance with the raw material ratio;

II. Polyoxyethylene castor oil (EL-40), fatty alcohol polyoxyethylene ether (AEO-09), sodium dodecyl sulfonate, tea saponin, fulvic acid, carboxymethyl chitosan and glycerol were added to a stirred tank, and then two thirds of the deionized water was poured into the stirred tank, and stirred until the materials dissolved, thereby obtaining solution A;

III. Emamectin benzoate was added to the solution A, and stirred until dissolved, thereby obtaining solution B;

IV. Hydroxyethyl cellulose dissolved in the residual water was added to the solution B, then 2,2',4,4'-tetrahydroxy benzophenone was added to and stirred at room temperature until dissolved, after which tributyl phosphate was added to, stirred thoroughly, allowed to stand still, and defoamed, thereby obtaining the title product.

The 1% multifunctional environmentally-friendly aqueous solution of emamectin benzoate prepared above was transparent and clear in appearance.

Example 10: A 3% Multifunctional Environmentally-Friendly Aqueous Solution of Emamectin Benzoate Raw material ratio is:

| | |
|---|---|
| emamectin benzoate | 3.0% (in percentage by weight, as follows); |
| ammonium tetradecyl sulphate | 4.5%; |
| fatty alcohol polyoxyethylene ether (AEO-15) | 3.0%; |
| tea saponin | 1.5%; |
| fulvic acid | 2.0%; |
| chitosan | 1.5%; |
| glycerol | 4.0%; |
| guar gum | 1.5%; |
| 2,4-dihydroxy-5-sulfo benzophenone | 0.3%; |
| organosilicone defoaming agent | 0.02%; and |
| deionized water | the remainder. |

10 kg of the title product with transparent appearance was obtained by a method similar to that described in Example 9.

Example 11: A 4% Multifunctional Environmentally-Friendly Aqueous Solution of Emamectin Benzoate Raw material ratio is:

| | |
|---|---|
| emamectin benzoate | 4% (in percentage by weight, as follows); |
| sodium tetradecyl ether sulphate | 6%; |
| fatty alcohol polyoxyethylene ether (AEO-20) | 2%; |
| alkyl polyglycoside | 2%; |
| tea saponin | 2%; |
| fulvic acid | 2%; |
| chitosan | 1.5%; |
| glycerol | 3.5%; |
| guar gum | 1.5%; |
| 2,4-dihydroxy-5-sulfo benzophenone | 0.4%; |
| organosilicone defoaming agent | 0.02%; and |
| deionized water | the remainder. |

1 kg of the title product with transparent appearance was obtained by a method similar to that described in Example 9.

Example 12: A 5% Multifunctional Environmentally-Friendly Aqueous Solution of Emamectin Benzoate Raw material ratio is:

| | |
|---|---|
| emamectin benzoate | 5% (in percentage by weight, as follows); |
| potassium hexadecyl ether sulphate | 7.5%; |
| fatty alcohol polyoxyethylene ether (AEO-20) | 2.5%; |
| alkyl polyglycoside | 2.5%; |
| tea saponin | 2%; |
| fulvic acid | 2%; |
| chitosan | 2%; |
| glycerol | 3.5%; |
| guar gum | 2%; |
| 2,4-dihydroxy-5-sulfo benzophenone | 0.5%; |
| organosilicone defoaming agent | 0.02%; and |
| deionized water | the remainder. |

1 kg of the title product with transparent appearance was obtained by a method similar to that described in Example 9.

Example 13: A 7% Multifunctional Environmentally-Friendly Aqueous Solution of Emamectin Benzoate Raw material ratio is:

| | |
|---|---|
| emamectin benzoate | 7.0%; |
| sodium ricinoleate | 3%; |
| sodium tetradecyl sulphate | 7%; |
| fatty alcohol polyoxyethylene ether (AEO-20) | 2%; |
| carboxymethyl chitosan | 2%; |
| tea saponin | 2%; |
| fulvic acid | 2%; |
| chitosan | 2%; |
| ethylene glycol | 3.0%; |
| organosilicone defoaming agent | 0.02%; and |
| deionized water | the remainder. |

1000 kg of the title product was obtained by a method similar to that described in Example 9.

Example 14: A 1% Multifunctional Environmentally-Friendly Aqueous Solution of Emamectin Benzoate Raw material ratio is:

| | |
|---|---|
| emamectin benzoate | 1.0% (in percentage by weight, as follows); |
| potassium oleate | 1.5%; |
| polyoxyethylene castor oil (EL-40) | 0.5%; |
| tea saponin | 1%; |
| fulvic acid | 1.5%; |
| chitosan | 0.5%; |
| glycerol | 5%; |
| hydroxyethyl cellulose | 2%; |
| 2,2',4,4'-tetrahydroxy benzophenone | 0.1%; |
| tributyl phosphate | 0.02%; and |
| deionized water | the remainder. |

1000 kg of the title product was obtained by a method similar to that described in example 9.

Example 15: A 3% Multifunctional Environmentally-Friendly Aqueous Solution of Emamectin Benzoate Raw material ratio is:

| | |
|---|---|
| emamectin benzoate | 3.0%; |
| sodium ricinoleate | 1.5%; |
| ammonium tetradecyl sulphate | 3.0%; |
| alkyl polyglycoside | 1.0% |
| fatty alcohol polyoxyethylene ether (AEO-15) | 1.0%; |
| Tea saponin | 1.5%; |
| fulvic acid | 2%; |
| chitosan | 1.5%; |
| glycerol | 4%; |
| guar gum | 1.5%; |
| 2,4-dihydroxy-5-sulfo benzophenone | 0.3%; |
| organosilicone defoaming agent | 0.02%; and |
| deionized water | the remainder. |

1000 kg of the title product was obtained by a method similar to that described in Example 9.

Example 16: A Multifunctional Environmentally-Friendly Water Soluble Powder of Emamectin Benzoate Raw materials are (in kg):

| | |
|---|---|
| emamectin benzoate | 5; |
| sodium dodecyl sulfonate | 5; |
| ammonium hexadecyl ether sulphate | 2.5; |
| fatty alcohol polyoxyethylene ether (AEO-20) | 2.5; |
| alkyl polyglycoside | 2.5; |
| tea saponin | 2; |
| fulvic acid | 2; |
| chitosan | 1.5; |
| guar gum | 1.5; |
| 2,4-dihydroxy-5-sulfo benzophenone | 0.5; and |
| organosilicone defoaming agent | 0.02. |

Sodium dodecyl sulfonate and ammonium hexadecyl ether sulphate were added to a stirred tank, then 50 kg of deionized water was added in and stirred at room temperature until the materials dissolved. Then AEO-20, alkyl polyglycoside, tea saponin, fulvic acid, chitosan and glycerol were added in and stirred at room temperature, thereby obtaining solution A. After that, emamectin benzoate was added to the solution A and stirred at room temperature until dissolves. Then hydroxyethyl cellulose and 2,4-dihydroxy-5-sulfo benzophenone which were dissolved in 25 kg of water were added in and stirred at room temperature until dissolved, thereby obtaining solution B. Organosilicone defoaming agent was added to the solution B, stirred slightly, allowed to stand still, and filtered, thereby obtaining solution C containing 5% emamectin benzoate which was clear in appearance.

Figure 2:
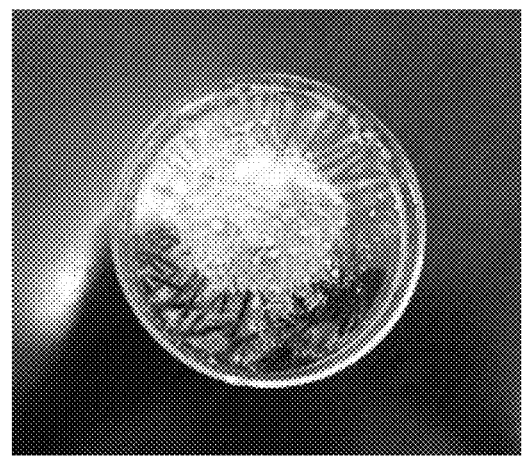
FIG. 2 is a photograph of the environmentally-friendly water soluble powder of emamectin benzoate prepared in Example 16.

The solution C was spray dried and an environmentally-friendly water soluble powder of emamectin benzoate with average particle size of 50-150 μm was obtained. Sample of the product was shown in FIG. 2. The content of emamectin benzoate in the water soluble powder was about 20%.

Example 17: A Multifunctional Environmentally-Friendly Water Soluble Powder of Emamectin Benzoate Raw materials are (in g):

| | |
|---|---|
| emamectin benzoate | 3; |
| sodium tetradecyl sulphate | 4.5; |
| fatty alcohol polyoxyethylene ether (AEO-15) | 3; |
| chitosan | 1.5; |
| fulvic acid | 2; |
| tea saponin | 1.5; |
| guar gum | 1.5; |
| 2,4-dihydroxy-5-sulfo benzophenone | 0.3; and |
| organosilicone defoaming agent | 0.02. |

A multifunctional environmentally-friendly water soluble powder of emamectin benzoate with average particle size of 50-150 μm was obtained by a method similar to that described in Example 16. Differences of the method used in this Example from that described in Example 16 lie in that: 55 g of deionized water was added to when the solution A was prepared, and 30 g of deionized water was added to when the solution B was prepared.

Figure 3:
FIG. 3 is a photograph of a 3% water solution of emamectin benzoate obtained by dissolving the multifunctional environmentally-friendly water soluble power of emamectin benzoate prepared in Example 17 in water.

Water was added to the obtained product and stirred slightly, to make a clear and transparent solution of emamectin benzoate in a concentration of 3% by weight, as shown in FIG. 3.

Example 18: A Multifunctional Environmentally-Friendly Water Soluble Powder of Emamectin Benzoate Raw materials are (in g):

| | |
|---|---|
| emamectin benzoate | 4; |
| sodium tetradecyl ether sulfonate | 6; |
| fatty alcohol polyoxyethylene ether (AEO-20) | 2; |
| alkyl polyglycoside | 2; |
| chitosan | 1.5; |
| fulvic acid | 2; |
| tea saponin | 2; |
| guar gum | 1.5; |
| 2,4-dihydroxy-5-sulfo benzophenone | 0.4; and |
| organosilicone defoaming agent | 0.02. |

A multifunctional environmentally-friendly water soluble powder of emamectin benzoate with average particle size of 50-150 μm was obtained by a method similar to that described in Example 17.

Example 19: A Multifunctional Environmentally-Friendly Water Soluble Powder of Emamectin Benzoate Raw materials are (in g):

| | |
|---|---|
| emamectin benzoate | 5; |
| ammonium hexadecyl ether sulphate | 6; |
| fatty alcohol polyoxyethylene ether (AEO-20) | 2.5; |
| alkyl polyglycoside | 2.5 |
| chitosan | 2; |
| fulvic acid | 2; |
| tea saponin | 2; |
| guar gum | 2; |
| 2,4-dihydroxy-5-sulfo benzophenone | 0.5; and |
| organosilicone defoaming agent | 0.02. |

A multifunctional environmentally-friendly water soluble powder of emamectin benzoate with average particle size of 50-150 μm was obtained by a method similar to that described in Example 17.

Figure 4:
FIG. 4 is a photograph of a 5% water solution of emamectin benzoate obtained by dissolving the multifunctional environmentally-friendly water soluble power of emamectin benzoate prepared in Example 19 in water.

Water was added to the obtained product and stirred slightly, to make a clear and transparent solution of emamectin benzoate in a concentration of 5% by weight, as shown in FIG. 4.

Example 20: An Environmentally-Friendly Water Soluble Powder of Emamectin Benzoate Raw materials are (in g):

| | |
|---|---|
| emamectin benzoate | 7; |
| sodium ricinoleate | 3; |
| sodium tetradecyl sulphate | 7; |
| fatty alcohol polyoxyethylene ether (AEO-20) | 2; |
| carboxymethyl chitosan | 2; and |
| Organosilicone defoaming agent | 0.02. |

A multifunctional environmentally-friendly water soluble powder of emamectin benzoate with average particle size of 50-150 μm was obtained by a method similar to that described in Example 17.

Experiment 1: Tyndall Experiment
1.1 Environmentally-Friendly Aqueous Solution of Emamectin Benzoate of the Present Invention A conical flask containing the 1% multifunctional environmentally-friendly aqueous solution of emamectin benzoate prepared in Example 1 and a conical flask containing a 1% micro-emulsion of emamectin benzoate (Shandong**Chemical Co., Ltd., China) were stood side-by-side, and then the above two kind of liquids were irradiated by laser emitted from a laser pointer.

Figure 5:
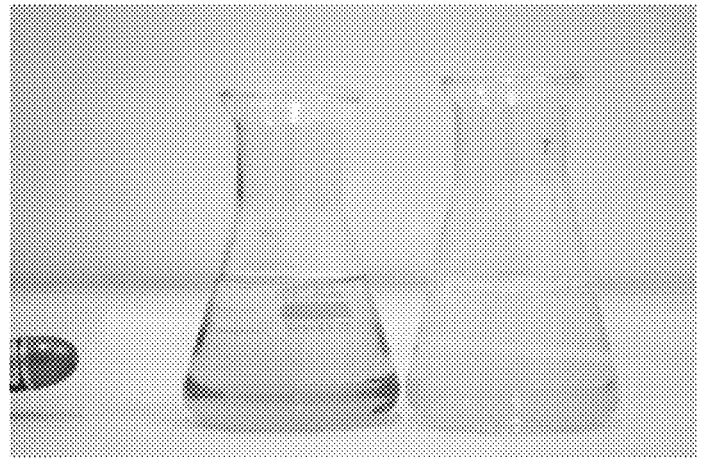
FIG. 5 is a photograph showing the Tyndall effect obtained in Experiment 1. In the photograph, in the left conical flask is the 1% environmentally-friendly aqueous solution of emamectin benzoate prepared in Example 1, and in the right is 1% micro-emulsion of emamectin benzoate.

Results were shown in FIG. 5. The laser passed through the aqueous solution prepared in Example 1 firstly, and essentially no "light path" appeared, which meant that the "tyndall effect" in the aqueous solution prepared in Example 1 was very weak. Afterwards, the laser with weakened intensity passed through the commercially available micro-emulsion subsequently, and apparent "light path" appeared, which meant the "tydall effect" was produced. The above results indicate that dispersion state in water of emamectin benzoate of the aqueous solution of emamectin benzoate prepared in Example 1 is smaller and more uniform than that of emamectin benzoate of the traditional micro-emulsion, and is closer to that of solution.

1.2 Multifunctional Environmentally-Friendly Aqueous Solution of Emamectin Benzoate of the Present Invention A conical flask containing the 1% multifunctional environmentally-friendly aqueous solution of emamectin benzoate prepared in Example 9 and a conical flask containing a 1% micro-emulsion of emamectin benzoate (Shandong**Chemical Co., Ltd., China) were stood side-by-side, and then the above two kind of liquids were irradiated by laser emitted from a laser pointer.

Figure 6:
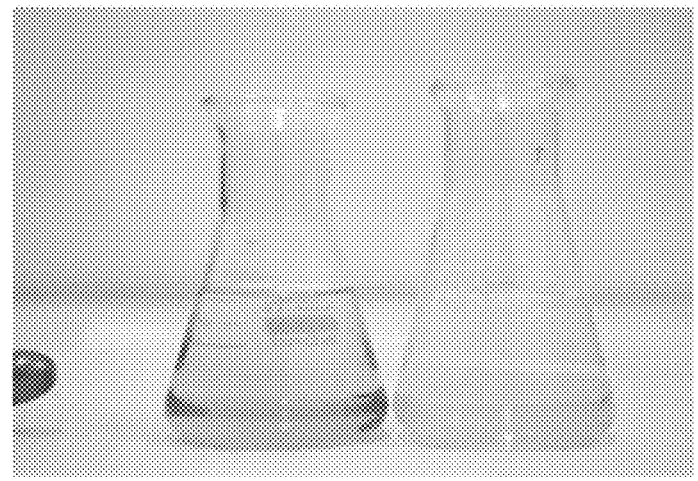
FIG. 6 is a photograph showing the Tyndall effect obtained in Experiment 1 In the photograph, in the left conical flask is the 1% environmentally-friendly aqueous solution of emamectin benzoate prepared in Example 9, and in the right is 1% micro-emulsion of emamectin benzoate.

Results were shown in FIG. 6. The laser passed through the aqueous solution prepared in Example 9 firstly, and essentially no "light path" appeared, which meant that the "tyndall effect" in the aqueous solution prepared in Example 9 was very weak. Afterwards, the laser with weakened intensity passed through the commercially available micro-emulsion subsequently, and apparent "light path" appeared, which meant the "tydall effect" was produced. The above results indicate that dispersion state in water of emamectin benzoate of the aqueous solution of emamectin benzoate prepared in Example 9 is smaller and more uniform than that of emamectin benzoate of the traditional micro-emulsion, and is closer to that of solution.

1.3 Water Solution of Environmentally-Friendly Water Soluble Power of Emamectin Benzoate of the Present Invention Multifunctional environmentally-friendly water soluble power of emamectin benzoate prepared in Example 16 was dissolved in water to prepare a water solution which was served as sample 1, and the concentration in percentage by weight of emamectin benzoate in the water solution is 1%. A 1% commercially available micro-emulsion of emamectin benzoate was served as sample 2. A conical flask containing sample 1 and a conical flask containing sample 2 were stood side-by-side, and then laser emitted from a laser pointer passed through sample 1 firstly and through sample 2 subsequently to observe whether a "light path" appeared in the two kind of liquids.

Figure 7:
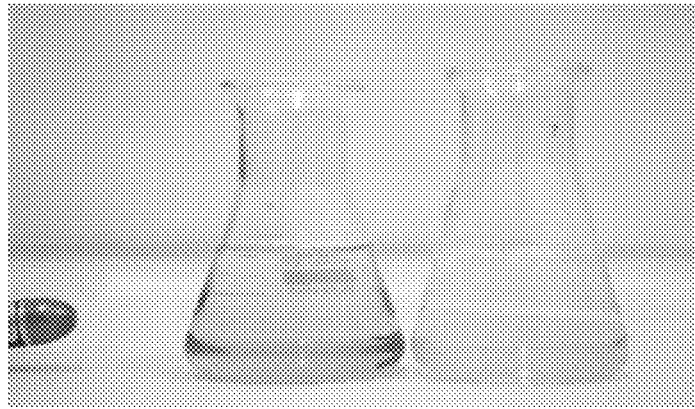
FIG. 7 is a photograph showing the Tyndall effect obtained in Experiment 1. In the photograph, in the left conical flask is sample 1, and in the right is sample 2.

Results were shown in FIG. 7. The laser passed through the liquid of sample 1 firstly, and essentially no "light path" appeared, which meant that the "tyndall effect" in sample 1 was very weak. Afterwards, the laser with weakened intensity passed through sample 2 having the same concentration subsequently, and apparent "light path" appeared, which meant the "tydall effect" was produced. The above results show that once the water soluble power of emamectin benzoate prepared in Example 16 is dissolved in water, dispersion state in water of emamectin benzoate is smaller and more uniform than that of emamectin benzoate of traditional micro-emulsion, and is closer to solution.

Experiment 2: Dissolution Experiment of Environmentally-Friendly Water Soluble Power of Emamectin Benzoate of the Present Invention 1) Environmentally-friendly water soluble power of emamectin benzoate prepared in Example 16 was added to a beaker containing 100 ml of water to make the concentration in percentage by weight of emamectin benzoate is 1%0.

Figure 8A:
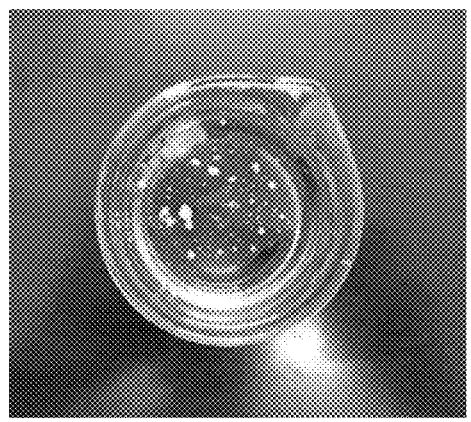
FIG. 8A is a photograph showing the multifunctional environmentally-friendly water soluble power of emamectin benzoate prepared in Example 16 which was just added to water.
Figure 8B:
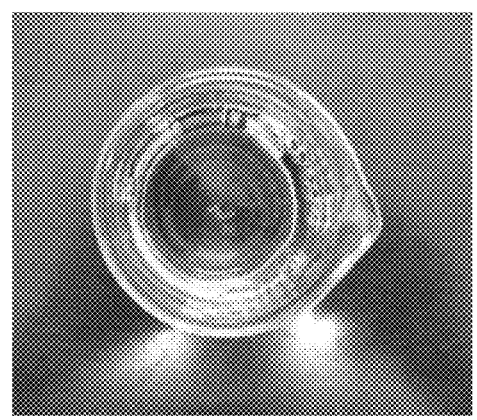
FIG. 8B is a photograph showing the environmentally-friendly water soluble power of emamectin benzoate prepared in Example 16 after being stirred slightly.
Figure 8C:
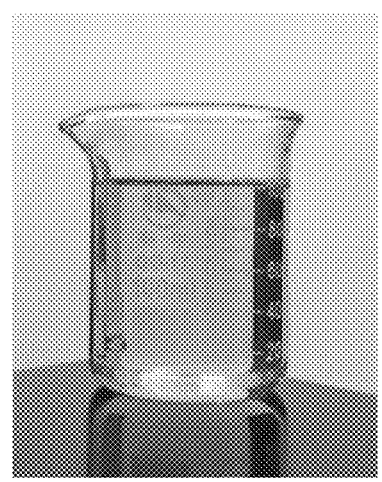
FIG. 8C is a photograph showing the Too water solution of emamectin benzoate prepared in Experiment 2.

As shown in FIG. 8A, when the water soluble power was added to water, it spread around on the water surface spontaneously and immediately and was infiltrated, and some masses of the power with larger volume floated on the water surface. As shown in FIG. 8B, the masses of the power dispersed and dissolved quickly after being slightly stirred with a glass rod, and a small amount of air bubbles which could burst by themselves formed on the edge of the solution. Finally, a clear and transparent solution as shown in FIG. 8C was obtained.

Conclusion: The environmentally-friendly water soluble power of emamectin benzoate prepared in Example 16 has a good water-solubility, and it can be quickly dissolved in water without any additives, which will result in a clear and transparent solution.

Experiment 3: Efficacy Experiment of Environmentally-Friendly Aqueous Solution of Emamectin Benzoate of the Present Invention Control of *Plutella xylostella* L. on Vegetables by a 3% Aqueous Solution of Emamectin Benzoate.

Crop: *Brassica oleracea* L.;
Object to be controlled: *Plutella xylostella* L.;
Experimental pesticidal formulation: The 3% environmentally-friendly aqueous solution of emamectin benzoate prepared in Example 3. Three dose groups were set as follows: the 3% environmentally-friendly aqueous solution of emamectin benzoate was diluted 2000, 1500 and 1000 times respectively;
Control pesticidal formulation: A commercially available 1% emulsifiable concentrate of emamectin benzoate which was diluted 500 times;
Application method and water consumption: spraying in 900 L/ha; and the pesticidal formulations were sprayed during the occurrence of numerous low instar larvae.
Experimental Results: See Table 2.

TABLE 2

Results of the efficacy experiment

| | | Control effect | | | |
|---|---|---|---|---|---|
| | Amount of effective | Quick efficacy (one day after applying) | | Persistent efficacy (seven days after applying) | |
| Pesticidal formulation | ingredient (mg/kg) | Control efficacy (%) | significance of difference | Control efficacy (%) | significance of difference |
| The 3% environmentally-friendly aqueous solution of | 15 | 18.00 | c | 41.69 | c |
| | 20 | 30.70 | b | 50.81 | b |
| | 30 | 51.83 | a | 82.94 | a |

TABLE 2-continued

Results of the efficacy experiment

| Pesticidal formulation | Amount of effective ingredient (mg/kg) | Control effect | | | |
|---|---|---|---|---|---|
| | | Quick efficacy (one day after applying) | | Persistent efficacy (seven days after applying) | |
| | | Control efficacy (%) | significance of difference | Control efficacy (%) | significance of difference |
| emamectin benzoate The 1% commercially available emulsifiable concentrate of emamectin benzoate | 20 | 29.73 | b | 42.81 | c |

Evaluation on Efficacy:

Results of that experiment show that, efficacies of the 3% environmentally-friendly aqueous solution of emamectin benzoate at three dose treatments for controlling *Plutella xylostella* L. on *Brassica oleracea* L. are 18.00%, 30.70% and 51.83% respectively one day after the pesticidal formulations were applied. The difference between the control efficacies of the three dose treatments are significant, wherein the control efficacy of the medium dose treatment was equal to that of the control pesticidal formulation, i.e. the 1% emulsifiable concentrate of emamectin benzoate which was diluted 500 times (29.73%). Control efficacies of various dose treatments of the experimental pesticidal formulation are from 41.69% to 82.94% seven days after the pesticidal formulations were applied. The difference between the control efficacies of the three dose treatments are significant, wherein the control efficacy of the low dose treatment was equal to that of the control pesticidal formulation, i.e. the 1% emulsifiable concentrate of emamectin benzoate which was diluted 500 times (42.81%); and the control efficacy of the medium dose treatment (50.81%) was higher than that of identical dose of the emulsifiable concentrate of emamectin benzoate.

Conclusion of the Experiment:

Although quick efficacy of the environmentally-friendly aqueous solution of emamectin benzoate of the present invention was equal to that of commercially available emulsifiable concentrate, the persistent efficacy of it was obviously stronger than that of commercially available emulsifiable concentrate. Therefore, the control efficacy for pests can be improved, and the spraying amount and frequency can be reduced by using the present formulation, leading to reduced total quantity of emamectin benzoate. What's more, the emulsifiable concentrate has a sharp odour for containing organic solvents, while the aqueous solution of the present invention does not have any stimulating odor. In summary, the aqueous solution of the present invention has higher efficacy, lower production costs and better environmental protection. Therefore, the aqueous solution of the present invention has significant advantages compared to the emulsifiable concentrate.

Experiment 4: Efficacy Experiment of Multifunctional Environmentally-Friendly Aqueous Solution of Emamectin Benzoate of the Present Invention Control of *Plutella xylostella* L. on vegetables by a 3% multifunctional environmentally-friendly aqueous solution of emamectin benzoate.

Crop: *Brassica oleracea* L.;

Object to be controlled: *Plutella xylostella* L.;

Experimental pesticidal formulation: The 3% multifunctional environmentally-friendly aqueous solution of emamectin benzoate prepared in Example 10. Three dose groups were set as follows: the 3% environmentally-friendly aqueous solution of emamectin benzoate was diluted 2000, 1500 and 1000 times respectively;

Control pesticidal formulation: A 1% commercially available emulsifiable concentrate of emamectin benzoate which was diluted 500 times; Application method and water consumption: spraying in 900 L/ha; and the pesticidal formulations were sprayed during the occurrence of numerous low instar larvae.

Experimental Results: See Table 3.

TABLE 3

Results of the efficacy experiment

| Pesticidal formulation | Amount of the effective ingredient (mg/kg) | Control effect | | | |
|---|---|---|---|---|---|
| | | Quick efficacy (one day after applying) | | Persistent efficacy (seven days after applying) | |
| | | Control efficacy (%) | significance of difference | Control efficacy (%) | significance of difference |
| The 3% multifunctional environmentally-friendly aqueous solution of emamectin benzoate | 15 | 18.21 | c | 42.87 | c |
| | 20 | 32.03 | b | 51.66 | b |
| | 30 | 52.67 | a | 83.49 | a |
| The 1% commercially available emulsifiable concentrate of emamectin benzoate | 20 | 29.73 | b | 42.81 | c |

Evaluation on Efficacy:

Results of that experiment show that, efficacies of the 3% multifunctional environmentally-friendly aqueous solution of emamectin benzoate at three dose treatments for controlling *Plutella xylostella* L. on *Brassica oleracea* L. are 18.21%, 32.03% and 52.67% respectively one day after the pesticidal formulations were applied. The difference between the control efficacies of the three dose treatments are significant, wherein the control efficacy of the medium dose treatment was equal to that of the control formulation, i.e. the 1% emulsifiable concentrate of emamectin benzoate which was diluted 500 times (29.73%). Control efficacies of various dose treatments of the experimental pesticidal formulation are from 42.87% to 83.49% seven days after the pesticidal formulations were applied. The difference between the control efficacies of the three dose treatments are significant, wherein the control efficacy of the low dose treatment was equal to that of the control pesticidal formulation, i.e. the 1% emulsifiable concentrate of emamectin benzoate which was diluted 500 times (42.81%): and the control efficacy of the medium dose treatment (55.66%) was higher than that of identical dose of the emulsifiable concentrate of emamectin benzoate.

What's more, leaves of *Plutella xylostella* L. of the three dose treatment groups of the multifunctional aqueous solution were fat and moist. When the 120 days of growth period completed, average yield of the three treatment groups was 5.2% higher than that of treatment group of 1% emulsifiable concentrate of emamectin benzoate.

Conclusion of the Experiment:

Although quick efficacy of the environmentally-friendly aqueous solution of emamectin benzoate of the present invention was equal to that of commercially available emulsifiable concentrate, the persistent efficacy of it was obviously stronger than that of commercially available emulsifiable concentrate. Therefore, the control efficacy for pests can be improved, and the spraying amount and frequency can be reduced by using the present formulation, leading to reduced total quantity of emamectin benzoate. In addition, the multifunctional environmentally-friendly aqueous solution of emamectin benzoate of the present invention can promote the growth of the plant it works on obviously.

Experiment 5: An Indoor Insecticidal Activity Test of Multifunctional Environmentally-Friendly Water Soluble Power of Emamectin Benzoate 1. Experimental Conditions:

1.1 Object to be tested: *Chilo suppressalis* Walker. The *Chilo suppressalis* Walker collected from rice field of Gaochun County in Jiangsu, China was reared in-house, and the 4-day larvae were used for testing.

1.2 Culture conditions: The *Chilo suppressalis* Walker was reared in-house by rice seedlings. The room-temperature, relative humidity and illumination time of the insectary were 28±2° C., more than 70% and 14 h respectively. Pot cultured rice seedlings were placed in an insect rearing cage sized in 30 cm×30 cm×50 cm for *Chilo suppressalis* Walker adults to lay eggs. Rice seeds of Liangyou Peijiu were sowed in a jar after accelerating germination, and the egg masses or larvae of *Chilo suppressalis* Walker were placed on the rice seedings with lengths of 5 cm-8 cm and reared. The 4-day larvae of *Chilo suppressalis* were used for testing.

1.3 Devices and tools: Scissor, brush pen, conical flask, beaker, cylinder, culture dish, pipet, tube of 3 cm×20 cm, cage for immersing insects, and clock.

2. Experimental Design 2.1 Experimental Pesticidal Formulation

A 5% multifunctional environmentally-friendly water solution of emamectin benzoate ("5% water solution of emamectin benzoate" for short) which was formulated by the multifunctional environmentally-friendly water soluble power of emamectin benzoate prepared in Example 16 and water;

A 1% emulsifiable concentrate of emamectin benzoate purchased from NANJING RED SUN CO., LTD., China.

2.2 Experimental Treatment 2.2.1 Dose Setting:

Preliminary experiments were conducted firstly. According to the results of the preliminary experiments, the 5% water solution of emamectin benzoate was formulated to solutions with five concentrations of 0.0025 mg/L, 0.005 mg/L, 0.01 mg/L, 0.02 mg/L and 0.04 mg/L respectively; and the 1% emulsifiable concentrate of emamectin benzoate was formulated to liquids with five concentrations of 0.0025 mg/L, 0.005 mg/L, 0.01 mg/L, 0.02 mg/L and 0.04 mg/L respectively.

2.2.2 Repeated Experiment

Each dose treatment was repeated in quadruplicate and about 15 4-day larvae were used in each repeated experiment.

2.3 Treatment Method 2.3.1 Treatment Time: 10 Seconds;

2.3.2 Insect Immersing and Seedling Immersing

About 30 days old rice seedlings were cut into rice straws of about 18 cm with short rice roots left, and the rice straws were washed and then dried out. Afterwards, the rice straws were immersed in one of the pesticidal solutions and liquids, taken out and dried out, and then placed in tube of 3 cm×20 cm containing a little water in the bottom. 4-day old larvae of *Chilo suppressalis* Walker were placed in one of the pesticidal solutions and liquids contained in the cage for immersing insect, and then taken out. The pesticidal solution or liquid on the surface of the larvae was soaked up, and then placed in the tube containing rice seedlings which were treated with corresponding concentration of pesticidal solution or liquid. Then the tube was sealed with a black cloth, and the larvae were transferred to the insectary for cultivation.

3. Experimental Method

The experiment was conducted with reference to "Pesticides guidelines for laboratory bioactivity tests Part 6: The immersion test for insecticide activity; Standard of agricultural industry of the People's Republic of China".

Treatment of the control group: Larvae of the control group were treated with deionized water without pesticides.

4. Method of Data Collection and Statistics 4.1 Data-collecting time: the experimental results were examined 72 h after pesticidal treatment.

4.2 Statistical Analysis of Data

The experiment was repeated if the mortality of the control group was more than 20%. However, if the mortality of the control group was lower than 20%, the mortalities of various treatment groups were corrected by use of Abbott formula. Toxicity regression equations were obtained by DPS Data Processing System and $LC_{50}$ and 95% confidence limit were calculated. Then statistical analysis was conducted.

Calculation Method:

$$\text{Corrected mortality \%} = \frac{\text{mortality of the treatment group} - \text{mortality of the control group}}{100 - \text{mortality of the control group}} \times 100$$

6. Analysis and Discussion of the Results

Figure 9:
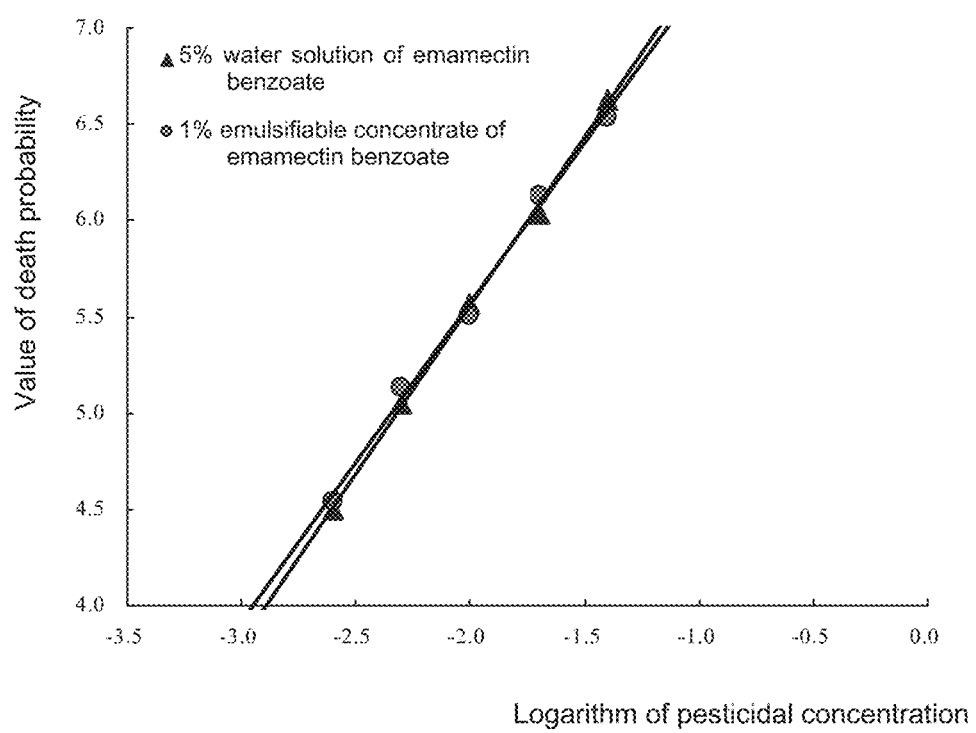
FIG. 9 shows regression lines of toxicity of the 5% water solution of emamectin benzoate and the 1% emulsifiable concentrate of emamectin benzoate in Experiment 5.

It can be seen from Table 4 that, tested concentrations of the 5% water solution of emamectin benzoate are same as those of 1% emulsifiable concentrate of emamectin benzoate. FIG. 9 reflects that the toxicity regression line of the 5% water solution of emamectin benzoate was interwoven with that of 1% emulsifiable concentrate of emamectin benzoate. What's more, Table 5 shows that $LC_{50}$ of 4-day larvae treated with 5% water solution of emamectin benzoate and $LC_{50}$ of 4-day larvae treated with 1% emulsifiable concentrate of emamectin benzoate, which are 0.0048 mg/L and 0.0046 mg/L respectively, are close to each other; and $LC_{90}$ of 4-day larvae treated with 5% water solution of emamectin benzoate and $LC_{90}$ of 4-day larvae treated with 1% emulsifiable concentrate of emamectin benzoate are 0.0262 mg/L and 0.0268 mg/L respectively. Therefore, analysis of DPS Data Processing System showed that there was no significant difference between the indoor insecticidal activity of 5% water solution of emamectin benzoate and 1% emulsifiable concentrate of emamectin benzoate for *Chilo suppressalis* Walker.

7. Conclusions of the Experiment

The experimental results showed that the indoor insecticidal activity of the 5% water solution of emamectin benzoate and the 1% emulsifiable concentrate of emamectin benzoate for 4-day larvae of *Chilo suppressalis* Walker are close to each other, and analysis of DPS Data Processing System showed that toxicity of the 5% water solution of emamectin benzoate for *Chilo suppressalis* Walker was comparable to that of the 1% emulsifiable concentrate of emamectin benzoate. Therefore, there was no significant difference in the indoor insecticidal activity of the 5% aqueous solution of emamectin benzoate and the 1% emulsifiable concentrate of emamectin benzoate for *Chilo suppressalis* Walker.

In conclusion, the present invention provides a novel formulation of emamectin benzoate. The formulation can be a liquid formulation which contains no toxic or harmful organic solvents and is good for environment protection. In addition, the present formulation can also be a solid formulation which is easy to transport and storage, and a clear solution which is thermodynamic stable, convenient to spray and produce efficacy can be obtained when the solid formulation is dissolved in water. Further, the aqueous solution of the present invention has higher efficiency and significant advantages compared with existing emulsifiable concentrate.

TABLE 4

Experimental results of indoor insecticidal activity of 5% water solution of emamectin benzoate for *Chilo suppressalis* Walker

| Tested pesticidal formulation | Concentration (mg/L) | Number of tested insects | Number of dead insects | Mortality (%) | Corrected mortality (%) |
|---|---|---|---|---|---|
| 5% water solution of emamectin benzoate | 0.04 | 60 | 57 | 95.00 | 94.70 |
|  | 0.02 | 62 | 53 | 85.48 | 84.61 |
|  | 0.01 | 65 | 47 | 72.31 | 70.65 |
|  | 0.005 | 60 | 32 | 53.33 | 50.53 |
|  | 0.0025 | 64 | 21 | 32.81 | 28.78 |
| 1% emulsifiable concentrate of emamectin benzoate | 0.04 | 66 | 62 | 93.94 | 93.58 |
|  | 0.02 | 64 | 56 | 87.50 | 86.75 |
|  | 0.01 | 64 | 45 | 70.31 | 68.53 |
|  | 0.005 | 62 | 35 | 56.45 | 53.84 |
|  | 0.0025 | 64 | 22 | 34.38 | 30.44 |
| Control | 0 | 63 | 2 | 3.17 | / |

TABLE 5

Calculation results of indoor insecticidal activity of 5% water solution of emamectin benzoate for *Chilo suppressalis* Walker

| Tested pesticidal formulation | Toxicity regression equation (y = a + bx) | $LC_{50}$ (mg/L) | 95% confidence limit (mg/L) | $LC_{90}$ (mg/L) |
|---|---|---|---|---|
| 5% water solution of emamectin benzoate | y = 9.0329 + 1.7401x | 0.0048 a | 0.0034 – 0.0062 | 0.0262 a |
| 1% emulsifiable concentrate of emamectin benzoate | y = 5.1133 + 1.6377x | 0.0046 a | 0.0032 – 0.0059 | 0.0268 a |

It is noted that in the above Tables, different letters in the same column mean the 5% level of significant difference has been reached among treatment groups; and same letters in the same column mean 5% level of significant difference has not been reached among treatment groups.

What is claimed:

1. An environmentally-friendly formulation of emamectin benzoate, wherein the formulation is an aqueous solution, in percentage by weight, consisting of: 1%-7% of emamectin benzoate, 1%-10% of agent A, 1%-6% of agent B, 1%-6% of an antifreezing agent, 0.01%-0.1% of a defoaming agent, and a remainder being water;
  wherein the agent A is one or more anionic surfactants having Formula 1:

$$CH_3(CH_2)_n(OCH_2CHR')_mRM \quad (1)$$

wherein in Formula 1,
  n=11, 13, 15 or 17;
  R'=H or $CH_3$;
  R=$-SO_3^-$, $-OSO_3^-$, $-SO_4^-$, $-OSO_4^-$, or $-CO_2^-$;
  m=0, 1, 2, 3, or 4; and
  M=$H^+$, $K^+$, $Na^+$, or $NH_4^\pm$
  wherein the agent B is a nonionic surfactant containing ethylene oxide unit, propylene oxide unit or glucose unit, or high molecular surfactant selected from the group consisting of water soluble starch derivatives, water soluble cellulose derivatives, chitosan, and chitosan derivatives;
  wherein the defoaming agent is one or more agents selected from the group consisting of organosilicone defoaming agent, $C_7$-$C_9$ fatty alcohol and tributyl phosphate; and
  wherein the antifreezing agent, other than the agent B, is one or more agents selected from the group consisting of ethylene glycol, propylene glycol, glycerol, polyethylene glycol and sorbitol.

2. The formulation according to claim 1, wherein the formulation is an aqueous solution, in percentage by weight, consisting of: 1%-7% of emamectin benzoate, 2%-8% of the agent A, 1%-6% of the agent B, 1%-6% of the antifreezing agent, 0.01%-0.1% of the defoaming agent, and the remainder being water.

3. The formulation according to claim 1, wherein the antifreezing agent is one or more agents selected from the group consisting of glycerol, ethylene glycol and propylene glycol.

4. An environmentally-friendly formulation of emamectin benzoate, wherein the formulation is a water soluble powder consisting of: 1-7 parts by weight of emamectin benzoate, 1-10 parts by weight of agent A, 1-6 parts by weight of agent B, and 0.01-0.1 parts by weight of a defoaming agent;
  wherein the agent A is one or more anionic surfactants having Formula 1:

$$CH_3(CH_2)_n(OCH_2CHR')_mRM \quad (1)$$

wherein in Formula 1,
  n=11, 13, 15 or 17;
  R'=H or $CH_3$;
  R=$-SO_3^-$, $-OSO_3^-$, $-SO_4^-$, $-OSO_4^-$, or $-CO_2^-$;
  m=0, 1, 2, 3, or 4; and
  M=$H^+$, $K^+$, $Na^+$, or $NH_4^\pm$
  wherein the agent B is a nonionic nonionic surfactant containing ethylene oxide unit, propylene oxide unit or glucose unit, or high molecular surfactant selected from the group consisting of water soluble starch derivatives, water soluble cellulose derivatives, chitosan, and chitosan derivatives; and
  wherein the defoaming agent is one or more selected from the group consisting of organosilicone defoaming agent, $C_7$-$C_9$ fatty alcohol and tributyl phosphate.

5. The formulation according to claim 4, wherein the formulation is a water soluble powder consisting of: 1-7 parts by weight of emamectin benzoate, 2-8 parts by weight of the agent A, 1-6 parts by weight of the agent B, and 0.01-0.1 parts by weight of the defoaming agent.

6. An environmentally-friendly formulation of emamectin benzoate, wherein the formulation is a multifunctional water soluble powder consisting of: 1-7 parts by weight of emamectin benzoate, 1-10 parts by weight of agent A, 1-6 parts by weight of agent B, 1-5 parts by weight of a functionalizing agent, 0.1-0.4 parts by weight of a light stabilizer, 1-3 parts by weight of a drift control agent, and 0.01-0.1 parts by weight of a defoaming agent;
  wherein the agent A is one or more anionic surfactants having Formula 1:

$$CH_3(CH_2)_n(OCH_2CHR')_mRM \quad (1)$$

wherein in Formula 1,
  n=11, 13, 15 or 17;
  R'=H or $CH_3$;
  R=$-SO_3^-$, $-OSO_3^-$, $-SO_4^-$, $-OSO_4^-$, or $-CO_2^-$;
  m=0, 1, 2, 3, or 4; and
  M=$H^+$, $K^+$, $Na^+$, or $NH_4^\pm$
  wherein the agent B is a nonionic surfactant containing ethylene oxide unit, propylene oxide unit or glucose unit, or a high molecular surfactant selected from the group consisting of water soluble starch derivatives, water soluble cellulose derivatives, chitosan, and chitosan derivatives;
  wherein the functionalizing agent, other than the emamectin benzoate, the agent A, the agent B, the light stabilizer, the drift control agent, and the defoaming agent, is selected from the group consisting of synthetic chemicals and natural products having a synergic, antibacterial or stress-resistance function, or having a role in stimulating crop growth, improving pesticide efficacy, reducing residual toxicity or improving quality of agricultural products;
  wherein the light stabilizer is one or more agents selected from the group consisting of salicylate light stabilizer, benzophenone light stabilizer, benzotriazole light stabilizer and hindered amine light stabilizer;
  wherein the drift control agent, other than the emamectin benzoate, the agent A, the agent B, the functionalizing agent, the light stabilizer, and the defoaming agent, is selected from the group consisting of water soluble synthetic materials and water soluble natural materials, and both materials can decrease surface tension of spray droplets, increase viscoelasticity, increase the deposition of pesticides, and/or reduce rebounce of droplets; and
  wherein the defoaming agent is one or more agents selected from the group consisting of organosilicone defoaming agent, $C_7$-$C_9$ fatty alcohol and tributyl phosphate.

7. The formulation according to claim 6, wherein the formulation is a multifunctional water soluble powder consisting of: 1-7 parts by weight of emamectin benzoate, 2-8 parts by weight of the agent A, 1-6 parts by weight of the agent B, 1-5 parts by weight of the functionalizing agent, 0.1-0.4 parts by weight of the light stabilizer, 1-3 parts by weight of the drift control agent, and 0.01-0.1 parts by weight of the defoaming agent.

8. A method for preparing the formulation according to claim 1, comprising the following steps:
  (I) adding defined amounts of the agent A, agent B, and antifreezing agent to a stirred tank, and then pouring part of the water to the stirred tank, and stirring until the agents dissolved, thereby obtaining solution A;

(II) adding defined amount of emamectin benzoate to the solution A, and stirring until dissolved, thereby obtaining solution B; and (III) adding remaining water to the solution B, stirring, and then adding defined amount of the defoaming agent, stirring slightly, and standing, followed by filtration to obtain the formulation of claim 1.

9. A method for preparing the formulation according to claim 4, comprising the following process I or process II:

wherein the process I comprises mixing defined amounts of emamectin benzoate, agent A, agent B, and the defoaming agent homogeneously to obtain the formulation of claim 4; or wherein process II comprises dissolving defined amount of the agent A in water, and then adding defined amount of emamectin benzoate, agent B, the defoaming agent and water to obtain a solution of emamectin benzoate in a concentration in percentage by weight of 1%-7%, and dehydrating the solution to obtain the formulation of claim 4.

10. The method according to claim 9, wherein the process II comprises the following steps:

(a) dissolving the agent A in 20-60 parts by weight of water, and stirring until dissolved, thereby obtaining solution A;

(b) adding the emamectin benzoate and the agent B to the solution A, and then adding further water to obtain a solution of emamectin benzoate in the concentration in percentage by weight of 1%-7%, and stirring until dissolved, thereby obtaining solution B;

(c) adding the defoaming agent to the solution B, stirring slightly, and standing before filtration, thereby obtaining solution C; and (d) spray drying the solution C to obtain the formulation of claim 4.

11. The formulation according to claim 1, wherein the nonionic surfactant is one or more agents selected from the group consisting of straight chain fatty alcohol polyoxyethylene ether, polyoxyethylene straight chain fatty acid ester, straight chain fatty amine polyoxyethylene ether, polyoxyethylene sorbitan fatty acid ester, alkyl polyglycoside and polyoxyethylene castor oil.

12. The formulation according to claim 2, wherein the nonionic surfactant is one or more agents selected from the group consisting of straight chain fatty alcohol polyoxyethylene ether, polyoxyethylene straight chain fatty acid ester, straight chain fatty amine polyoxyethylene ether, polyoxyethylene sorbitan fatty acid ester, alkyl polyglycoside and polyoxyethylene castor oil.

13. The formulation according to claim 4, wherein the nonionic surfactant is one or more agents selected from the group consisting of straight chain fatty alcohol polyoxyethylene ether, polyoxyethylene straight chain fatty acid ester, straight chain fatty amine polyoxyethylene ether, polyoxyethylene sorbitan fatty acid ester, alkyl polyglycoside and polyoxyethylene castor oil.

14. The formulation according to claim 5, wherein the nonionic surfactant is one or more agents selected from the group consisting of straight chain fatty alcohol polyoxyethylene ether, polyoxyethylene straight chain fatty acid ester, straight chain fatty amine polyoxyethylene ether, polyoxyethylene sorbitan fatty acid ester, alkyl polyglycoside and polyoxyethylene castor oil.

15. The formulation according to claim 6, wherein the nonionic surfactant is one or more agents selected from the group consisting of straight chain fatty alcohol polyoxyethylene ether, polyoxyethylene straight chain fatty acid ester, straight chain fatty amine polyoxyethylene ether, polyoxyethylene sorbitan fatty acid ester, alkyl polyglycoside and polyoxyethylene castor oil.

16. The formulation according to claim 7, wherein the nonionic surfactant is one or more agents selected from the group consisting of straight chain fatty alcohol polyoxyethylene ether, polyoxyethylene straight chain fatty acid ester, straight chain fatty amine polyoxyethylene ether, polyoxyethylene sorbitan fatty acid ester, alkyl polyglycoside and polyoxyethylene castor oil.

17. The formulation according to claim 1, wherein the high molecular surfactant is one or more agents selected from the group consisting of dextrin, carboxymethyl starch, carboxymethyl cellulose, chitosan, carboxymethyl chitosan, and chitosan quaternary ammonium salt.

18. The formulation according to claim 2, wherein the high molecular surfactant is one or more agents selected from the group consisting of dextrin, carboxymethyl starch, carboxymethyl cellulose, chitosan, carboxymethyl chitosan, and chitosan quaternary ammonium salt.

19. The formulation according to claim 4, wherein the high molecular surfactant is one or more agents selected from the group consisting of dextrin, carboxymethyl starch, carboxymethyl cellulose, chitosan, carboxymethyl chitosan, and chitosan quaternary ammonium salt.

20. The formulation according to claim 5, wherein the high molecular surfactant is one or more agents selected from the group consisting of dextrin, carboxymethyl starch, carboxymethyl cellulose, chitosan, carboxymethyl chitosan, and chitosan quaternary ammonium salt.

21. The formulation according to claim 6, wherein the high molecular surfactant is one or more agents selected from the group consisting of dextrin, carboxymethyl starch, carboxymethyl cellulose, chitosan, carboxymethyl chitosan, and chitosan quaternary ammonium salt.

22. The formulation according to claim 7, wherein the high molecular surfactant is one or more agents selected from the group consisting of dextrin, carboxymethyl starch, carboxymethyl cellulose, chitosan, carboxymethyl chitosan, and chitosan quaternary ammonium salt.

23. The formulation according to claim 2, wherein the antifreezing agent is one or more agents selected from the group consisting of glycerol, ethylene glycol and propylene glycol.

24. The formulation according to claim 6, wherein the functionalizing agent is one or more agents selected from the group consisting of tea saponin, humic acid, chitosan or derivatives thereof, alginate, hyaluronic acid, saponin extract, and matrine.

25. The formulation according to claim 7, wherein the functionalizing agent is one or more agents selected from the group consisting of tea saponin, humic acid, chitosan or derivatives thereof, alginate, hyaluronic acid, saponin extract, and matrine.

26. The formulation according to claim 6, wherein the light stabilizer is one or more agents selected from the group consisting of 2,4-dihydroxy-5-sulfo benzophenone, 2,2',4,4'-tetrahydroxy benzophenone, and 2,3,4,4'-tetrahydroxy benzophenone.

27. The formulation according to claim 7, wherein the light stabilizer is one or more agents selected from the group consisting of 2,4-dihydroxy-5-sulfo benzophenone, 2,2',4,4'-tetrahydroxy benzophenone, and 2,3,4,4'-tetrahydroxy benzophenone.

28. The formulation according to claim 6, wherein the drift control agent is one or more agents selected from the group consisting of water soluble cellulose derivatives, water soluble guar gum or derivatives thereof, and water soluble starch or derivatives thereof.

29. The formulation according to claim 7, wherein the drift control agent is one or more agents selected from the group consisting of water soluble cellulose derivatives, water soluble guar gum or derivatives thereof, and water soluble starch or derivatives thereof.

\* \* \* \* \*